(12) United States Patent
Zaiki et al.

(10) Patent No.: US 8,971,601 B2
(45) Date of Patent: Mar. 3, 2015

(54) MEDICAL IMAGE DIAGNOSIS DEVICE AND MEDICAL IMAGE PROCESSING METHOD

(75) Inventors: Ryuji Zaiki, Utsunomiya (JP); Yoshiyasu Hayashi, Nasushiobara (JP); Nobuo Kobayashi, Nasushiobara (JP); Teruomi Gunji, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 245 days.

(21) Appl. No.: 13/391,650

(22) PCT Filed: Oct. 13, 2011

(86) PCT No.: PCT/JP2011/005733
§ 371 (c)(1),
(2), (4) Date: Feb. 22, 2012

(87) PCT Pub. No.: WO2012/049851
PCT Pub. Date: Apr. 19, 2012

(65) Prior Publication Data
US 2012/0162222 A1   Jun. 28, 2012

(30) Foreign Application Priority Data
Oct. 14, 2010 (JP) ................................ 2010-231535

(51) Int. Cl.
*G06K 9/00* (2006.01)
*A61B 6/00* (2006.01)

(52) U.S. Cl.
CPC ................. *A61B 6/504* (2013.01); *A61B 6/463* (2013.01)
USPC ........................................................ 382/128

(58) Field of Classification Search
None
See application file for complete search history.

(56) References Cited

U.S. PATENT DOCUMENTS

| | | | |
|---|---|---|---|
| 7,876,879 B2* | 1/2011 | Morton | 378/57 |
| 8,774,560 B2* | 7/2014 | Sugaya et al. | 382/305 |

(Continued)

FOREIGN PATENT DOCUMENTS

| | | |
|---|---|---|
| JP | 2004 283325 | 10/2004 |
| JP | 2005 160503 | 6/2005 |

(Continued)

OTHER PUBLICATIONS

International Preliminary Report on Patentability and Written Opinion issued May 16, 2013, in International application No. PCT/JP2011/005733 (English translation only).

(Continued)

*Primary Examiner* — Shervin Nakhjavan
(74) *Attorney, Agent, or Firm* — Oblon, McClelland, Maier & Neustadt, L.L.P.

(57) ABSTRACT

A medical image diagnosis device according to an embodiment of the present invention includes: an imaging unit that takes an image of a subject, with an X-ray generation unit which exposes the subject to X-rays and an X-ray detector which detects X-rays that have passed through the subject, being supported on a supporter; a control unit that controls so as to rotate and move the supporter with respect to the subject and take images of the subject from a plurality of viewpoints; a storage unit that stores image data taken from a plurality of the viewpoints; an image processing unit that classifies a plurality of pieces of the image data stored in the storage unit into a plurality of imaging ranges to generate thumbnail images; and a display unit that displays thumbnail images generated by the image processing unit.

14 Claims, 10 Drawing Sheets

(56) References Cited

U.S. PATENT DOCUMENTS

| | | | |
|---|---|---|---|
| 2003/0095147 A1* | 5/2003 | Daw | 345/771 |
| 2004/0077952 A1* | 4/2004 | Rafter et al. | 600/481 |
| 2004/0161139 A1* | 8/2004 | Samara et al. | 382/131 |
| 2004/0186371 A1 | 9/2004 | Toda | |
| 2004/0236791 A1* | 11/2004 | Kinjo | 707/104.1 |
| 2006/0033728 A1* | 2/2006 | Sako | 345/204 |
| 2007/0032720 A1* | 2/2007 | Koivukangas et al. | 600/407 |
| 2007/0154075 A1* | 7/2007 | Matsumoto | 382/128 |
| 2007/0242069 A1* | 10/2007 | Matsue et al. | 345/428 |
| 2008/0247636 A1* | 10/2008 | Davis et al. | 382/152 |
| 2009/0043157 A1* | 2/2009 | Hirakawa et al. | 600/109 |
| 2010/0020917 A1* | 1/2010 | Gagliano | 378/4 |
| 2010/0077358 A1* | 3/2010 | Sugaya et al. | 715/838 |
| 2010/0189218 A1* | 7/2010 | Sakaguchi et al. | 378/62 |
| 2011/0286647 A1* | 11/2011 | Cao et al. | 382/131 |
| 2011/0317815 A1* | 12/2011 | Bernhardt et al. | 378/98.5 |
| 2012/0130167 A1* | 5/2012 | Coste-Maniere et al. | 600/109 |

FOREIGN PATENT DOCUMENTS

| | | |
|---|---|---|
| JP | 2006 235971 | 9/2006 |
| JP | 2007 37781 | 2/2007 |
| JP | 2008 29401 | 2/2008 |
| JP | 2008 220482 | 9/2008 |
| JP | 2008 245742 | 10/2008 |
| JP | 2009 148422 | 7/2009 |
| JP | 2010 82270 | 4/2010 |
| JP | 2010 125120 | 6/2010 |

OTHER PUBLICATIONS

International Search Report Issued Jan. 17, 2012 in PCT/JP11/05733 Filed Oct. 13, 2011.

* cited by examiner

FIG.8
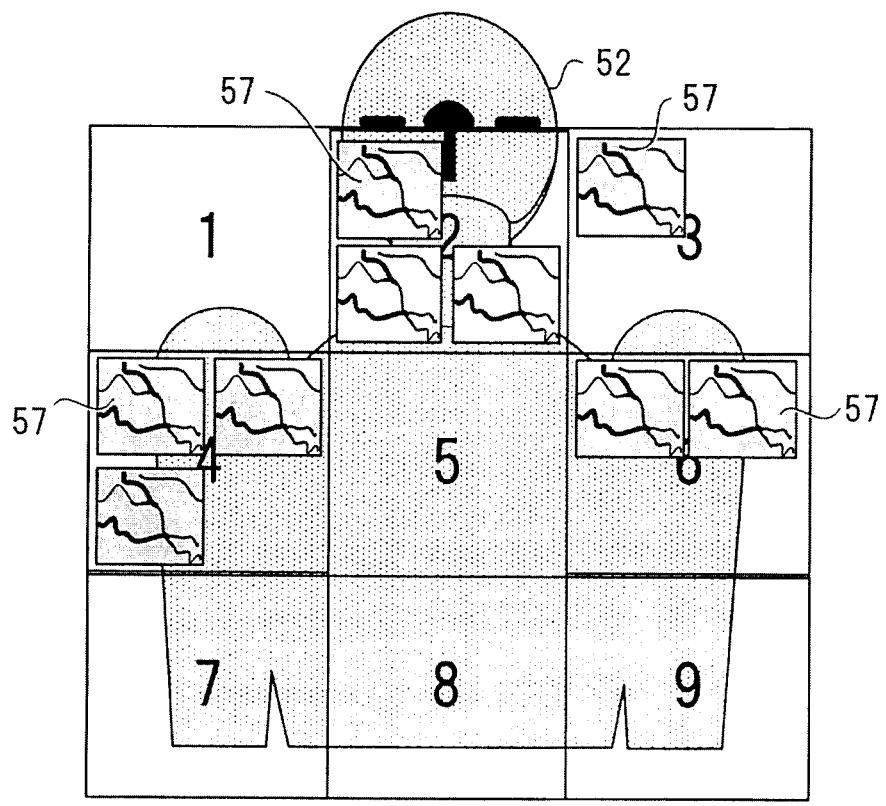
FIG.9
(a)
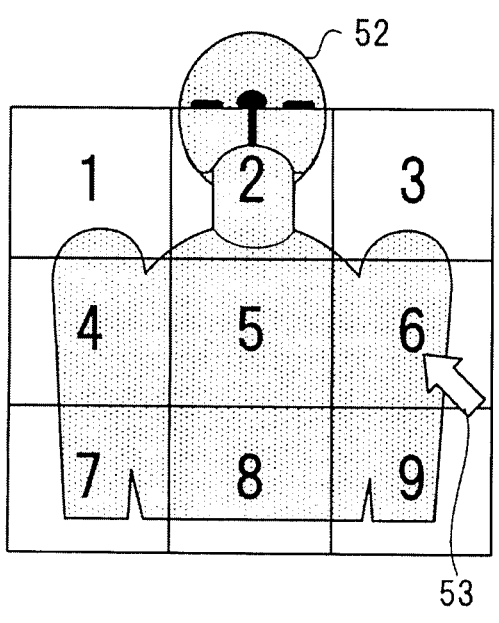
(b)
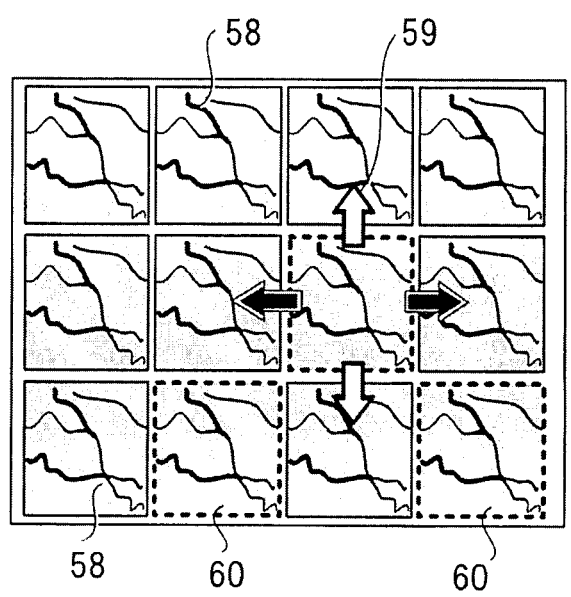

MEDICAL IMAGE DIAGNOSIS DEVICE AND MEDICAL IMAGE PROCESSING METHOD

TECHNICAL FIELD

Embodiments of the present invention relate to a medical image diagnosis device and medical image processing method that are able to classify images taken from a plurality of viewpoints into a plurality of imaging ranges displaying, and to observe.

BACKGROUND ART

A conventional medical image diagnosis device (an angiography device, for example) includes an X-ray generation unit, which generates X-rays for a subject P, and an X-ray detection unit, which detects X-rays that have passed through the subject in a two-dimensional manner to generate X-ray projection data. The X-ray generation unit and the X-ray detection unit are supported by an arm (generally referred to as a C-arm). As the C-arm moves in the direction of a body axis of the subject on a bed or rotates around the body axis of the subject, it is possible to take images of the subject from various directions.

By the way, when images taken by the conventional medical image diagnosis device are observed, thumbnail images are arranged and displayed, for example, in the order the images are taken, and an arbitrary image is specified from among the above images to display the detailed image. However, when there are a large number of images taken from a plurality of angular directions, it takes time to determine which image has been taken at what angle if thumbnail images are simply arranged and displayed in order of imaging history. Usually, when a determination is made as to at what angle an image has been taken, the determination needs to be made by seeing the image (the shape of a blood vessel, for example), or the angle needs to be identified from supplementary information (angular information) of the image. The problem is that as the number of images collected increases, it takes time to find an image that a user wants to see.

CITATION LIST

Patent Literature

PTL 1: Japanese Patent Application Laid-Open No. 2004-283325
PTL 2: Japanese Patent Application Laid-Open No. 2006-235971

SUMMARY OF THE INVENTION

Technical Problem

An object to be achieved by the present invention is to provide a medical image diagnosis device and medical image processing method that classify thumbnail images into a plurality of imaging ranges and display the thumbnail images, thereby saving the effort of finding a required image.

Solution to Problem

A medical image diagnosis device of an embodiment includes: an imaging unit that takes an image of a subject, with an X-ray generation unit which exposes the subject to X-rays and an X-ray detector which detects X-rays that have passed through the subject, being supported on a supporter; a control unit that controls so as to rotate and move the supporter with respect to the subject and take images of the subject from a plurality of viewpoints; a storage unit that stores image data taken from a plurality of the viewpoints; an image processing unit that classifies a plurality of pieces of the image data stored in the storage unit into a plurality of imaging ranges to generate thumbnail images; and a display unit that displays thumbnail images generated by the image processing unit.

BRIEF DESCRIPTION OF THE DRAWINGS

FIG. 8 is an explanatory diagram showing another example in which thumbnail images are attached to a 2D human body model.
FIG. 9 is an explanatory diagram showing one example of displaying a 2D human body model and a table of thumbnail images.

DESCRIPTION OF EMBODIMENTS

Hereinafter, a medical image diagnosis device of an embodiment of the present invention will be described in detail with reference to the accompanying drawings. Incidentally, in each diagram, the same parts are denoted by the same reference symbols.

(First Embodiment)

Figure 1:
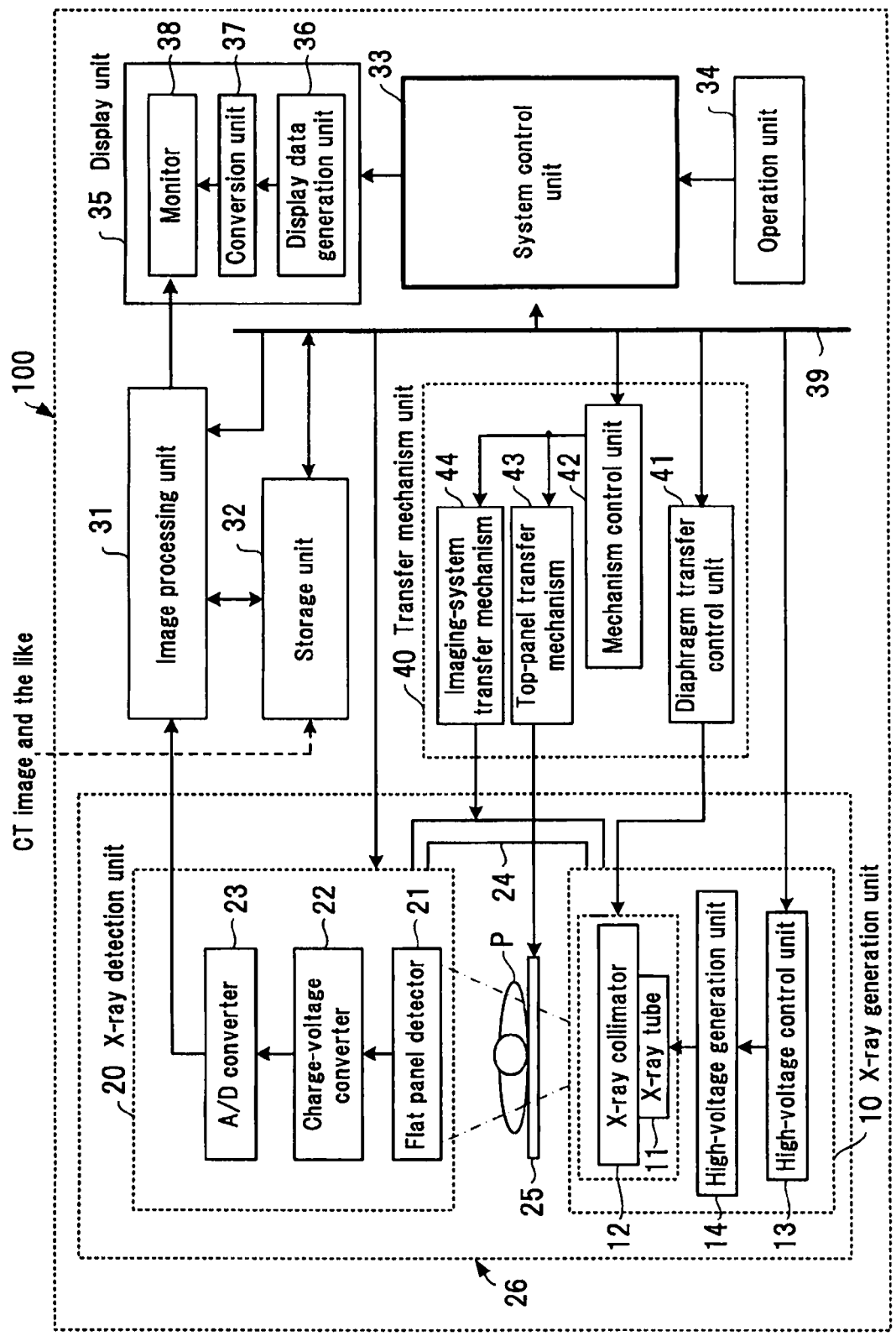
FIG. 1 is a block diagram showing the configuration of a medical image diagnosis device according to an embodiment.

FIG. 1 is a block diagram showing the configuration of a medical image diagnosis device according to an embodiment. The medical image diagnosis device shown in FIG. 1 is, for example, an X-ray image diagnosis device 100 called an angiography device. The X-ray image diagnosis device 100 includes an X-ray generation unit 10, which generates X-rays for a subject P, and an X-ray detection unit 20, which detects X-rays that have passed through the subject P in a two-dimensional manner and generates X-ray projection data on the basis of the detection results.

The X-ray generation unit 10 includes an X-ray radiation unit having an X-ray tube 11 and an X-ray collimator 12, a high-voltage control unit 13, and a high-voltage generation unit 14. The X-ray tube 11 is a vacuum tube that generates X-rays; the X-ray tube 11 generates X-rays by using a high voltage to cause electrons emitted from a cathode (filament) to accelerate and strike against a tungsten anode. The high-voltage control unit 13 controls the high-voltage generation unit 14 in accordance with an instruction signal from a system control unit 33 (described below), and takes control of X-ray radiation conditions, such as a tube current of the X-ray tube 11, a tube voltage, X-ray pulse width, a radiation cycle, an imaging section, and radiation time.

The X-ray detection unit 20 includes a flat panel detector 21, a charge-voltage converter 22, which converts a charge read from the flat panel detector 21 into a voltage, and an A/D converter 23, which converts an output of the charge-voltage converter 22 into digital signals. X-ray projection data are output from the A/D converter 23.

The X-ray generation unit 10 and the X-ray detection unit 20 are supported by an arm (C-arm) 24. The C-arm 24 is able to move in the direction of a body axis of the subject P placed on a top panel 25 of a bed and also able to rotate around the body axis of the subject P. Incidentally, the X-ray generation unit 10 and the X-ray detection unit 20 constitute an imaging unit 26. As the C-arm 24 rotates, the imaging unit 26 circles around the subject P and is able to take pictures of the subject P in a plurality of different angular directions.

The X-ray image diagnosis device 100 includes an image processing unit 31, a storage unit 32, the system control unit 33, an operation unit 34 and a display unit 35. The image processing unit 31 processes X-ray projection data from the A/D converter 23 to generate image data. For the generated image data, the image processing unit 31 performs image processing, such as edge enhancement and S/N improvement, when needed. The generated image data are stored in the storage unit 32.

The image processing unit 31 collects and classifies image data into imaging ranges, which are set in advance, stores the image data in the storage unit 32, and outputs the image data stored to the display unit 35 after turning the image data into thumbnails (described later in detail). The image data processed by the image processing unit 31, or the image data stored in the storage unit 32, are read when necessary, and supplied to the display unit 35 where the image data are displayed.

The system control unit 33 includes a CPU and a storage circuit (not shown), and makes up a control unit that takes overall control of each unit of the X-ray image diagnosis device 100 via a bus line 39 on the basis of input information, setting information and selection information supplied from the operation unit 34.

The operation unit 34 is designed to allow a doctor or any other user to input various commands or to do other operations, and has an interactive interface equipped with an input device, such as a mouse, keyboard, trackball or joystick, a display panel, various switches, or the like. The operation unit 34 is also used to set the traveling direction and speed of the top panel 25, to set the rotational/travelling direction and rotational/traveling speed of an imaging system, to set X-ray radiation conditions including a tube voltage and a tube current, and to perform other operations.

In order to display image data, the display unit 35 includes a display data generation unit 36, a conversion unit 37 and a monitor 38. The display data generation unit 36 synthesizes supplementary information with image data, and converts image data into a predetermined display format to generate display data. The conversion unit 37 performs D/A (Digital/Analog) conversion and television format conversion on display data to generate image signals, which are then displayed on the monitor 38 such as liquid crystal.

The X-ray image diagnosis device 100 includes a transfer mechanism unit 40. The transfer mechanism unit 40 includes a diaphragm transfer control unit 41 and a mechanism control unit 42. The diaphragm transfer control unit 41 controls the movements of diaphragm blades and the like in the X-ray collimator 12. The mechanism control unit 42 performs transfer control of a transfer mechanism 43 for the top panel 25 on which the subject P is placed, and of an imaging-system transfer mechanism 44. The transfer mechanism unit 40 runs as the operation unit 34 is operated, and performs transfer control of each part under the control of the system control unit 33.

Figure 2:
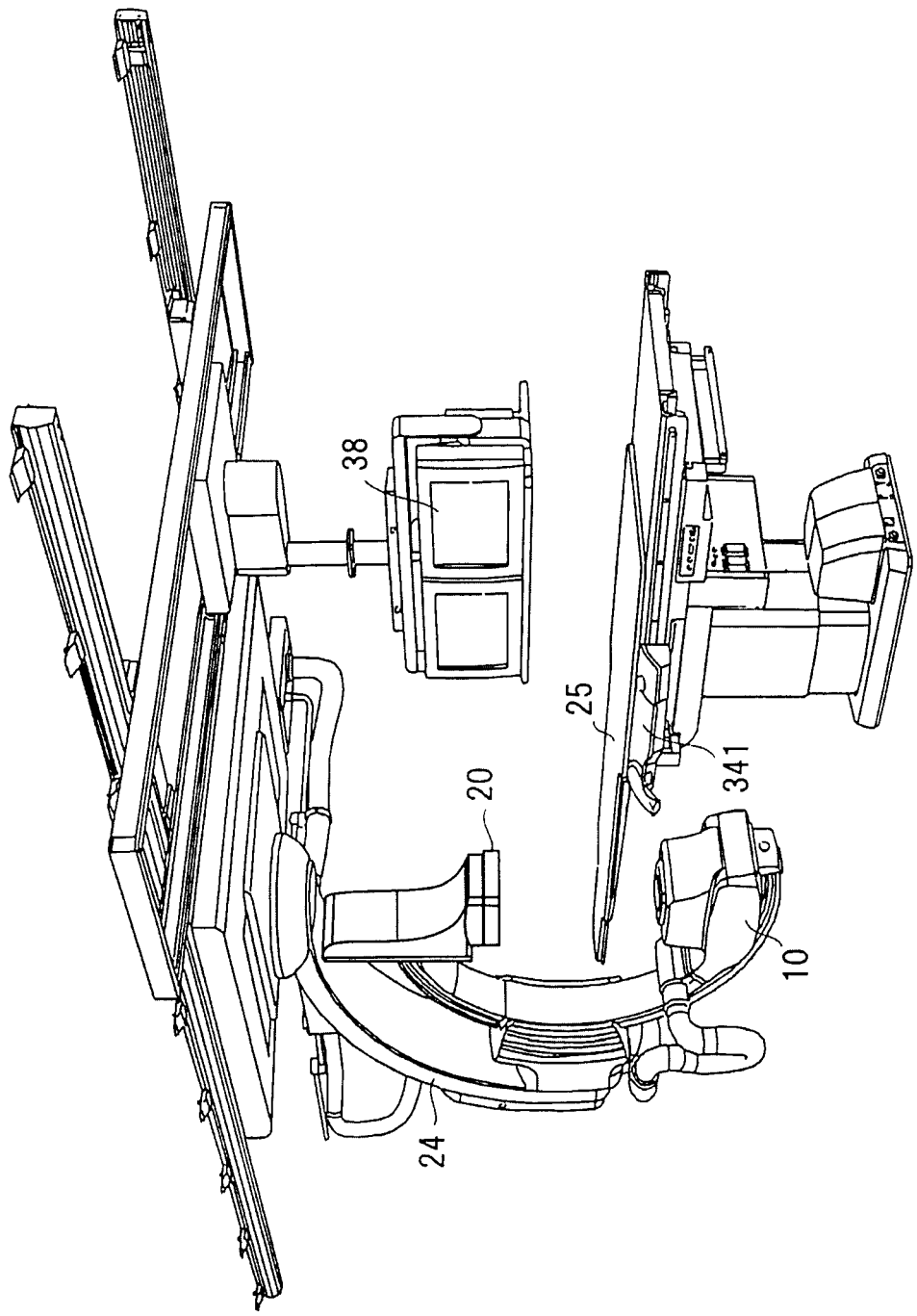
FIG. 2 is a perspective view showing the overall configuration of an X-ray image diagnosis device according to one embodiment.

FIG. 2 is a perspective view showing the overall configuration of the X-ray image diagnosis device 100 (angiography device). In FIG. 2, the X-ray generation unit 10 and the X-ray detection unit 20 are supported by the C-arm 24 in such a way that the X-ray generation unit 10 and the X-ray detection unit 20 face each other. Moreover, a bed is disposed relative to the C-arm 24. On the top panel 25 of the bed, the subject (not shown) is placed. The position and height of the top panel 25 can be controlled by the mechanism control unit 42.

The C-arm 24 is supported for example by rails, which are provided on a ceiling section, and able to move in the direction of the body axis of the subject from the head (Cranial) to the leg (Caudal). As the C-arm 24 rotates, the imaging unit 26 (the X-ray generation unit 10 and the X-ray detection unit 20) rotates around the body axis to circle around the subject. The imaging unit 26 is also able to slide and rotate along the C-arm 24.

X-ray projection data are processed by the image processing unit 31, and image data are displayed on the monitor 38. The monitor 38 is for example attached to the ceiling section. To the bed, an operation unit 341 is attached. In response to an operation of the operation unit 341, the system control unit 33 controls the height of the top panel 25, controls the movement and rotation of the C-arm 24, adjusts an X-ray irradiation range, controls an irradiation timing, and performs other processes.

The following describes a process by the image processing unit 31 of generating image data. According to the embodiment, image data taken from a plurality of viewpoints are classified into a plurality of imaging ranges, and thumbnail images are generated. If an imaging range is specified and if there are image data in the corresponding imaging range, then thumbnails of the image data are displayed. For example, if a user specifies an arbitrary angular direction from among image data taken and if there are image data taken from the corresponding angular direction, then thumbnails of the image data are displayed. Alternatively, if a position on the body-axis direction of the subject is specified as an imaging range and if there are image data taken at the specified position, then thumbnails of the image data are displayed. Moreover, when the angular direction or the position on the body-axis direction is specified, a 3D or 2D human body model is displayed.

Figure 3:
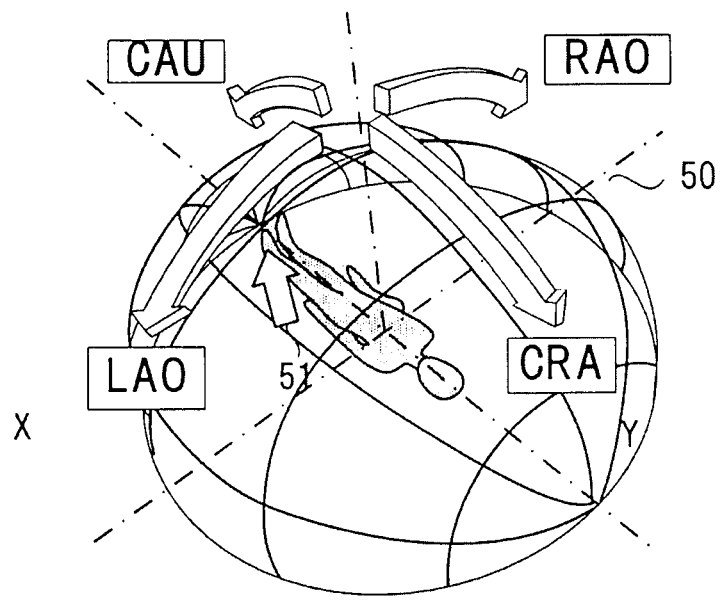
FIG. 3 is an explanatory diagram showing a 3D human body model.

FIG. 3 is a diagram showing an example of a 3D human body model 50 (three-dimensional coordinates). With the 3D human body model 50 being displayed on a screen, it is possible to specify a viewpoint direction in order to view image data taken from the viewpoint direction. For example, when a mouse is operated to move a cursor 51 onto an arbitrary position of the 3D human body model 50 and is clicked, the position of the cursor 51 makes it possible to specify an imaging range (imaging angle). Image data taken from the corresponding angular direction are read from the storage unit 32 and turned into thumbnails. The thumbnail images are displayed on a display screen.

As for information about at which imaging angle the image data are taken, the following and other values are recorded at the time of imaging, the angle of the C-arm 24, the position of the arm (the position of the ceiling), the position of the bed, and the position and direction of a patient. The above recorded information (supplementary information) is stored together with the image data. The imaging angle is determined based on the supplementary information. The image processing unit 31 classifies, on the basis of the imaging angle, the image data into a plurality of imaging ranges, and generates thumbnail images.

Incidentally, in FIG. 3, CRA and CAU represent angles at which the C-arm 24 is rotated in a cranio-caudal direction around a left-and-right direction X of the patient, with CRA indicating the cranium (Cranial) and CAU the cauda (Caudal). LAO and RAO represent angles at which the C-arm 24 is rotated in the left-and-right direction around the cranio-caudal direction Y of the patient, with LAO indicating a left anterior oblique position (Left Anterior Oblique) and RAO a right anterior oblique position (Right Anterior Oblique). Thumbnails are miniature representations of files, such as images and documents.

What is explained in FIG. 3 is an example in which an imaging range is specified by operating the mouse and moving the cursor 51 to an arbitrary position of the human body model 50. However, a position seen from the front side of the human body model 50 may be specified as an imaging range by operating the mouse and rotating the displayed human body model 50 in an arbitrary angular direction.

Figure 4:
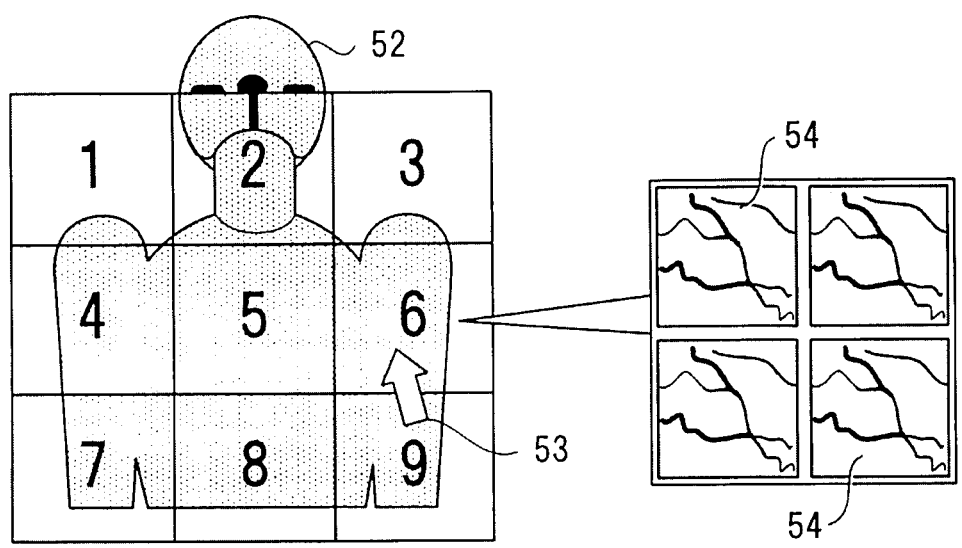
FIG. 4 is an explanatory diagram showing an imaging range selected with the use of a 2D human body model.

FIG. 4 shows a 2D human body model 52. The human body model 52 is divided into sections so as to look like a matrix, with numbers 1 to 9 assigned to the sections. The numbers 1 to 9 represent nine angular directions for taking images. For example, the number 5 indicates an angle of the right ahead direction of the subject P. The number 2 indicates an angle of CRA direction. The number 4 indicates an angle of RAO direction. The number 6 indicates an angle of LAO direction.

Then, when a mouse is operated to move a cursor 53 onto a frame of an arbitrary number of the 2D human body model 52 and is clicked, then an imaging range is specified. Image data taken from an angular direction specified by the corresponding number are extracted and turned into thumbnails. The thumbnail images are displayed on a display screen.

FIG. 4 shows four pieces of image data taken from an angular direction specified by the number 6, showing an example of four thumbnail images 54 displayed. Thumbnail images 54 are similarly displayed even when angular direction is specified using the 3D human body model 50 shown in FIG. 3.

Figure 5:
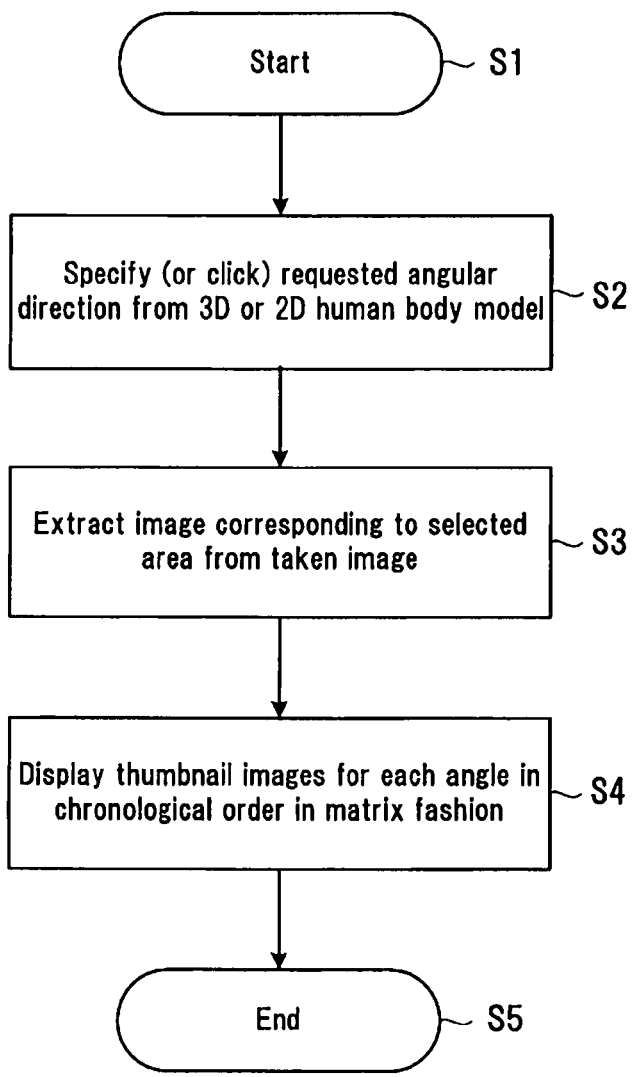
FIG. 5 is a flowchart showing a process of selecting an imaging range and displaying thumbnail images.

FIG. 5 is a flowchart showing a process of extracting, after an arbitrary angular direction is specified, corresponding images taken. Step S1 is a start step. At step S2, the 3D or 2D human body model 50 (or 52) is displayed on a display screen. For example, an imaging range is specified by operating a mouse to move the cursor 51 (or 53) to a position of a requested angle and clicking.

At step S3, from image data stored in the storage unit 32, the image data corresponding to the selected area (or image data taken from the requested angular direction) are retrieved so that the corresponding image data are extracted. At step S4, the extracted image data are turned by the image processing unit 31 into thumbnails, which are matrix-displayed in chronological order. The process comes to an end at step S5.

Incidentally, a plurality of thumbnail images 54 are arranged and disposed in chronological order, and a user selects an arbitrary image from among the above images. As a result, the selected taken image can be enlarged when being displayed on a screen. Moreover, the thumbnail images 54 are images taken from angular directions in which users want to view. Therefore, unlike the conventional method, it is possible to save the effort of making a determination as to which image has been taken at what angle.

Incidentally, what is explained in FIG. 4 is an example of specifying an arbitrary angular direction. However, a plurality of positions on the body-axis direction of the subject, as well as the angular direction, may be specified. For example, images may be taken at a plurality of positions spreading from the chest of the subject P to the lower leg. Accordingly, image data taken at a plurality of positions on the body-axis direction of the subject may be classified into a plurality of imaging ranges when being turned into thumbnails, and then the images may be displayed. When an imaging range is specified by operating the mouse, the cursor 51 is moved along the body-axis direction.

(Second Embodiment)

A second embodiment of the present invention will be described. According to the second embodiment, on the basis of angular information that supplementary information of image data taken contains, taken images are attached for each angle onto a 3D or 2D model. If there is a plurality of taken images at each angle, the images are displayed so as not to overlap.

Figure 6:
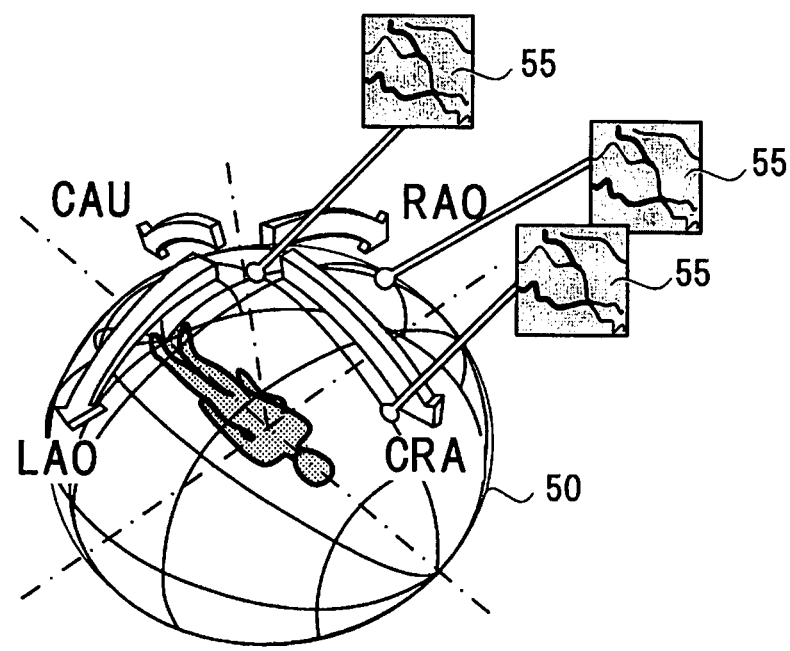
FIG. 6 is an explanatory diagram showing an example in which thumbnail images are attached to a 3D human body model.
Figure 7:
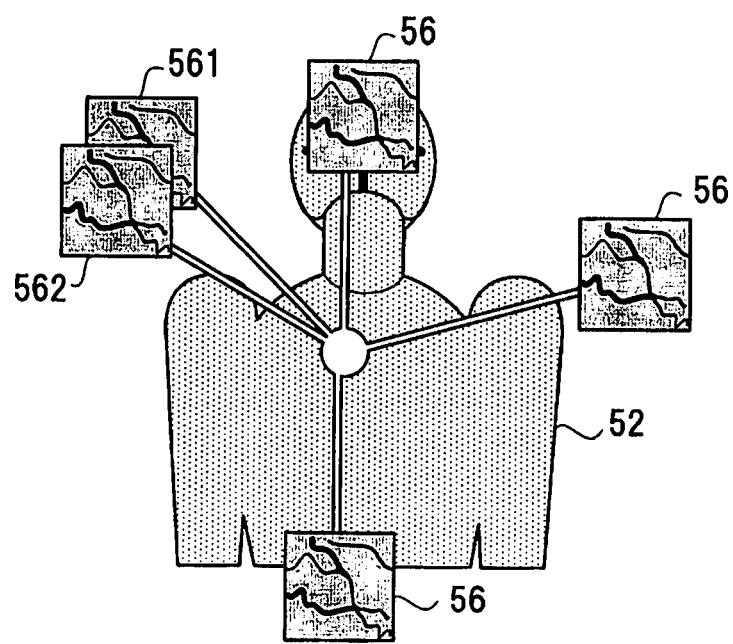
FIG. 7 is an explanatory diagram showing an example in which thumbnail images are attached to a 2D human body model.

FIG. 6 shows an example in which an imaging range (angular direction) is specified in the 3D human body model 50, images taken at each angle are turned into thumbnails, and a plurality of thumbnail images 55 taken in three directions are attached. FIG. 7 shows an example in which a specific region (the heart, for example) is specified, and, if there are images of the specific region taken from a plurality of angular directions, the images are turned into thumbnails, and a plurality of thumbnail images 56 are attached.

If there is a plurality of images taken at each angle, the images are displayed so as not to overlap completely. FIG. 7 shows an example in which, when there is a plurality of images taken from the same angle, the images are displayed at different locations as in the case of the thumbnail images 561 and 562. Therefore, it is possible to instantly figure out whether there is an image of a region that a user wants to view and at what angle the image has been taken.

FIG. 8 is an explanatory diagram showing another display example according to the second embodiment. FIG. 8 shows what is suitable for a display monitor having a large screen. What is shown is an example in which, within areas (or sections indicated by numbers 1 to 9) that indicate a plurality of imaging ranges on a human body model 52, taken images are each turned into thumbnails, and thumbnail images 57 are attached. If a plurality of images taken from the same angular direction exist, a plurality of thumbnail images 57 are attached in chronological order. If a large number of thumbnail images exist in one section, then thumbnail images are further reduced in size before being displayed.

Incidentally, thumbnail images 55, 56 and 57 may be attached to the human body model 50 (or 52) on a per-imaging-range basis. In this case, when a user selects an arbitrary image from among the above images, the selected taken image is enlarged and displayed on a screen.

(Third Embodiment)

A third embodiment of the present invention will be described. According to the third embodiment, images taken at each angle are displayed in the form of a matrix. An arbitrary thumbnail image is then selected, identified and displayed.

FIG. 9(a) shows an example in which a 2D human body model 52 is divided into sections so as to look like a matrix with numbers 1 to 9 attached, and an imaging range (angular direction) is selected by operating a mouse and moving a cursor 53 to a frame of an arbitrary number of the 2D human body model 52. As clicking is performed at a time when the cursor 53 is at an arbitrary position, an angular direction is selected. Image data within the selected imaging range are extracted and turned into thumbnails, and the thumbnail images are disposed on a display screen in chronological order.

FIG. 9(b) shows an example in which a plurality of pieces of image data corresponding to the No. 6 imaging range exist, and 12 thumbnail images 58 are displayed. Even when an angular direction is specified by the cursor 51 with the use of the 3D human body model 50 shown in FIG. 3, thumbnail images 58 are displayed as in the case of FIG. 9(b).

It is also possible to specify an arbitrary thumbnail image 58 by operating a mouse and moving a cursor 59 on thumbnail images in the vertical and horizontal directions. A thumbnail image specified by the cursor 59 becomes, for example, highlighted when being displayed so that the thumbnail image can be distinguished from other thumbnail images. The thumbnail images that become highlighted when being displayed are indicated by dotted lines 60. The thumbnail images, which become highlighted when being displayed, are sequentially enlarged and displayed in the order the images are taken.

Incidentally, when an image that will be highlighted when being displayed is selected, a number may be entered through a numerical keypad in a way that specifies numbers 1 to 9 of matrix-like sections.

Figure 10:
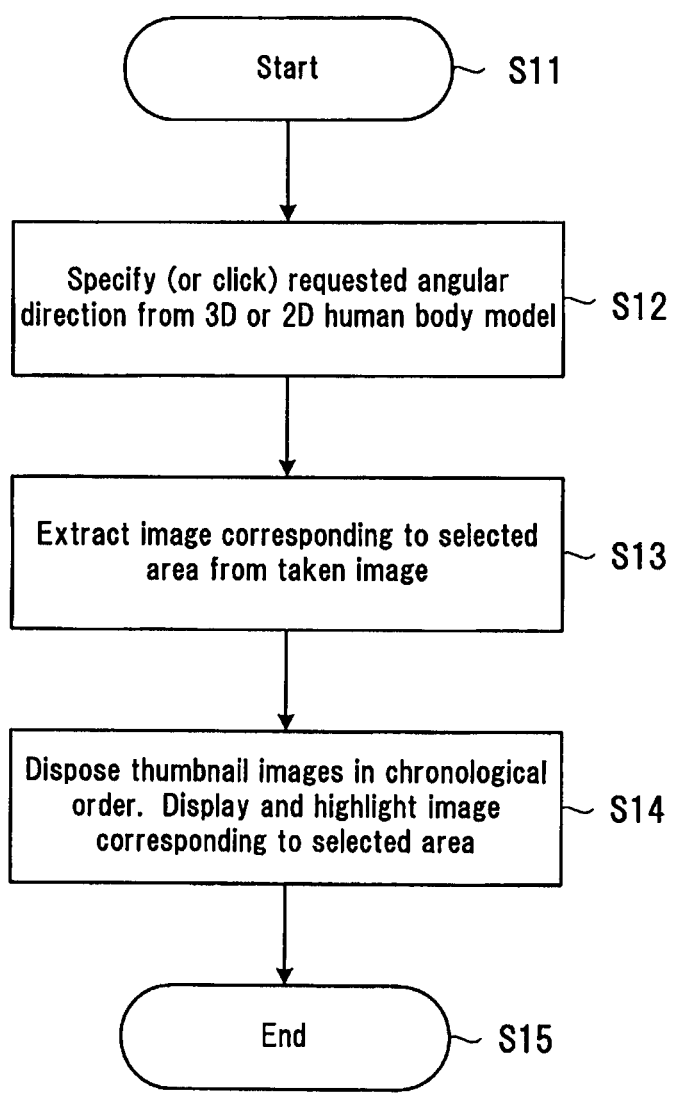
FIG. 10 is a flowchart showing a display process of FIG. 9.

FIG. 10 is a flowchart showing a process of highlighting, after an angular direction is specified, a corresponding image when the image is displayed, according to the third embodiment. Step S11 is a start step. At step S12, the 3D or 2D human body model 50 (or 52) is displayed on a display screen. For example, by operating the mouse, the cursor 51 (or 53) is moved to a position of a requested angle before clicking is performed.

At step S13, from image data stored in the storage unit 32, image data corresponding to a selected area (or image data taken from the requested angular direction) are retrieved, and the corresponding image data are extracted. At step S14, the extracted image data are turned by the image processing unit 31 into thumbnails, which are then disposed in chronological order and matrix-displayed. An arbitrary thumbnail image 58 is specified by the cursor 59. The thumbnail image corresponding to the selected area is highlighted when being displayed. The process comes to an end at step S15.

The images that are highlighted when being displayed are sequentially enlarged when being displayed in the order the images are taken. Therefore, if a plurality of images taken from an angular direction in which a user wants to view exist, it is possible to select an arbitrary image, which is then enlarged and displayed. In that manner, it becomes easier to find an image of a desired angle because the image becomes highlighted when being displayed.

(Fourth Embodiment)

A fourth embodiment of the present invention will be descried. According to the fourth embodiment, images taken at each of a plurality of angles are classified by region before being arranged and disposed in chronological order. At the same time, the images are displayed in such away that a comparison can be made between pre-treatment and post-treatment.

Figure 11:
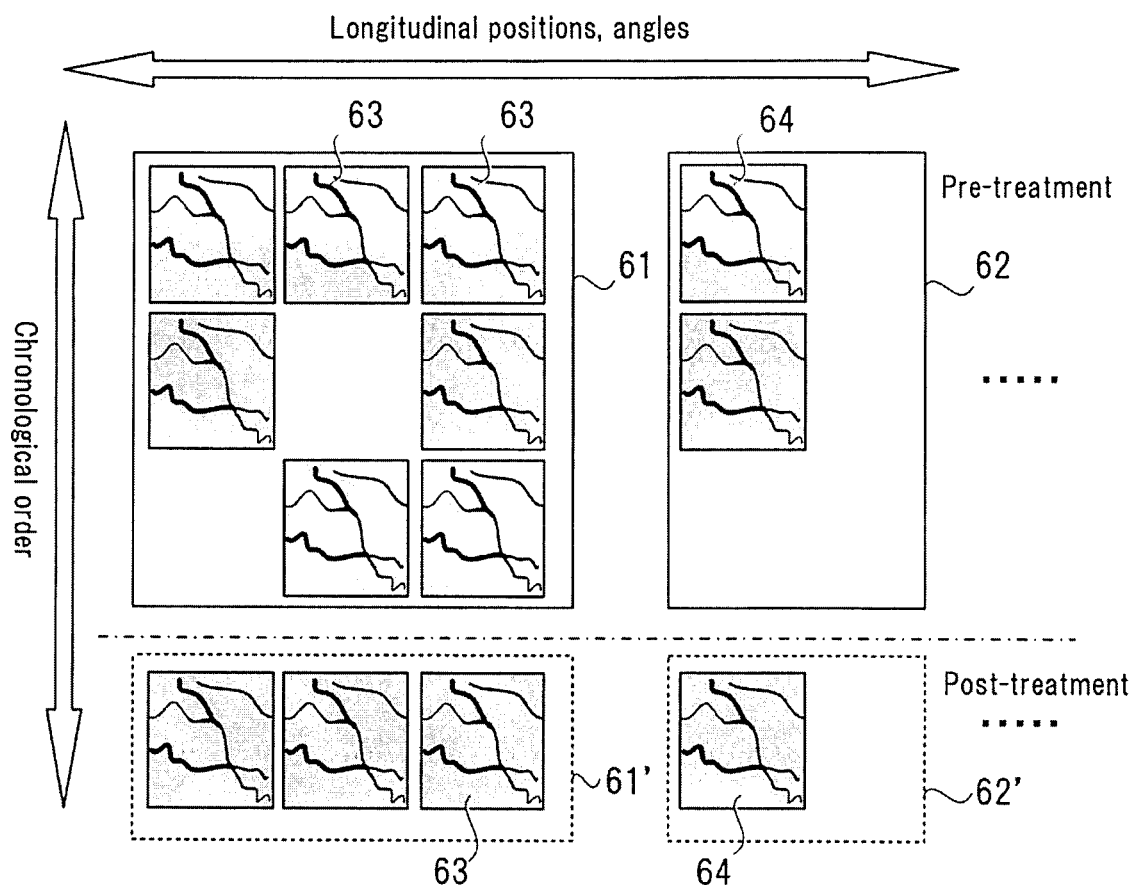
FIG. 11 is an explanatory diagram showing an example of arranging thumbnail images of each region on a per imaging-angle basis and displaying in chronological order.

In FIG. 11, taken images of each region of the subject P are turned into thumbnails on a horizontal axis, and are arranged and displayed on a per imaging-angle basis. For example, the horizontal axis represents longitudinal positions from the head to the lower leg, and is divided into sections including a first region 61, a second region 62, . . . , and images taken at each angle are turned into thumbnails, which are then arranged and displayed.

A vertical axis represents the chronological order, and is divided into sections including pre-treatment regions 61, 62, . . . and post-treatment regions 61', 62', . . . ; thumbnail images 63 and 64 are arranged and displayed. Incidentally, as for the chronological order, whether an image indicates pre-treatment or post-treatment may be determined based on an insertion device, such as a catheter, on the image or information about angiogram/blood flow and the like. Alternatively, a user may input pre-treatment or post-treatment time.

Images are displayed as shown in FIG. 11. Therefore, pre-treatment and post-treatment images can be displayed in a comparison form. When an arbitrary image is selected from among the thumbnail images 63 and 64, the selected taken image can be enlarged and displayed on a screen.

Figure 12:
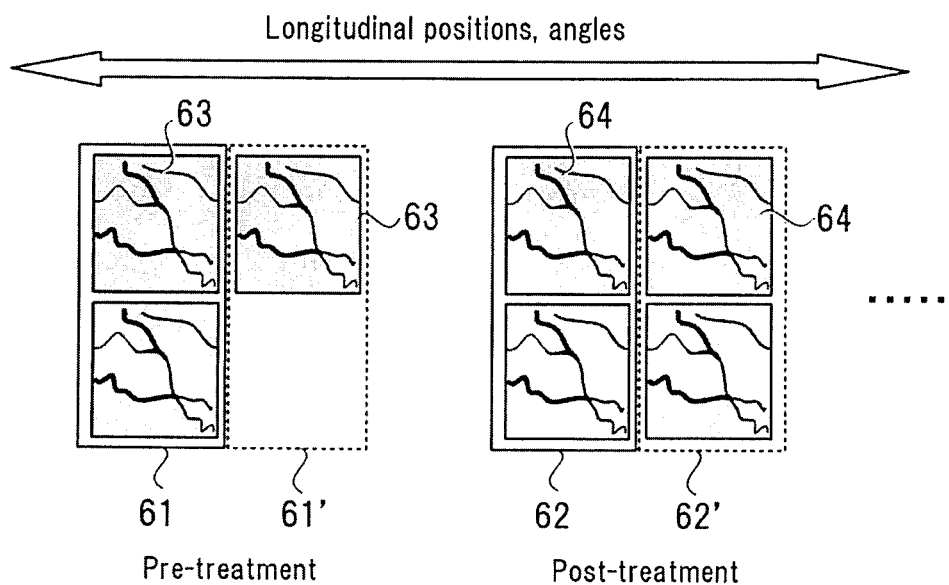
FIG. 12 is an explanatory diagram showing another display example instead of the displaying shown in FIG. 11.

FIG. 12 shows another display example of the fourth embodiment. Taken images of each region of the subject P are turned into thumbnails on a horizontal axis, and are arranged and displayed on a per imaging-angle basis. At the same time, pre-treatment and post-treatment images are arranged and displayed in a lateral direction. For example, the horizontal axis represents a direction from the head to the lower leg. As for a first region 61, a second region 62, . . . , images taken at each angle are turned into thumbnails and are arranged and displayed. At the same time, thumbnail images 63 and 64 of pre-treatment regions 61, 62, and post-treatment regions 61', 62', . . . are displayed side by side.

In that manner, taken images are arranged on a per-angle basis along longitudinal positions, and are matrix-displayed in chronological order. Moreover, the taken images are classified into pre-treatment and post-treatment sections (or according to the time set by a user) before being displayed. As a result, it becomes easier to find a desired image. Moreover, previous inspection results are similarly turned into thumbnails, which are then displayed. Therefore, it becomes easier to weigh inspection results against previous inspection results.

When inspection results are compared with previous inspection results, in addition to arranging and displaying pre-treatment and post-treatment thumbnail images, images taken before and after treatment may be arranged and displayed. For example, if there is only a small number of pre-treatment-taken images and post-treatment-taken images that are taken from the same angular direction (or if there is one image, for example), the pre-treatment-taken images and post-treatment-taken images may be simultaneously arranged and displayed without being turned into thumbnails. Alternatively, when a pre-treatment-taken images or post-treatment-taken image is selected from among thumbnail images, the other taken image may be simultaneously displayed in response to the selection.

Figure 13:
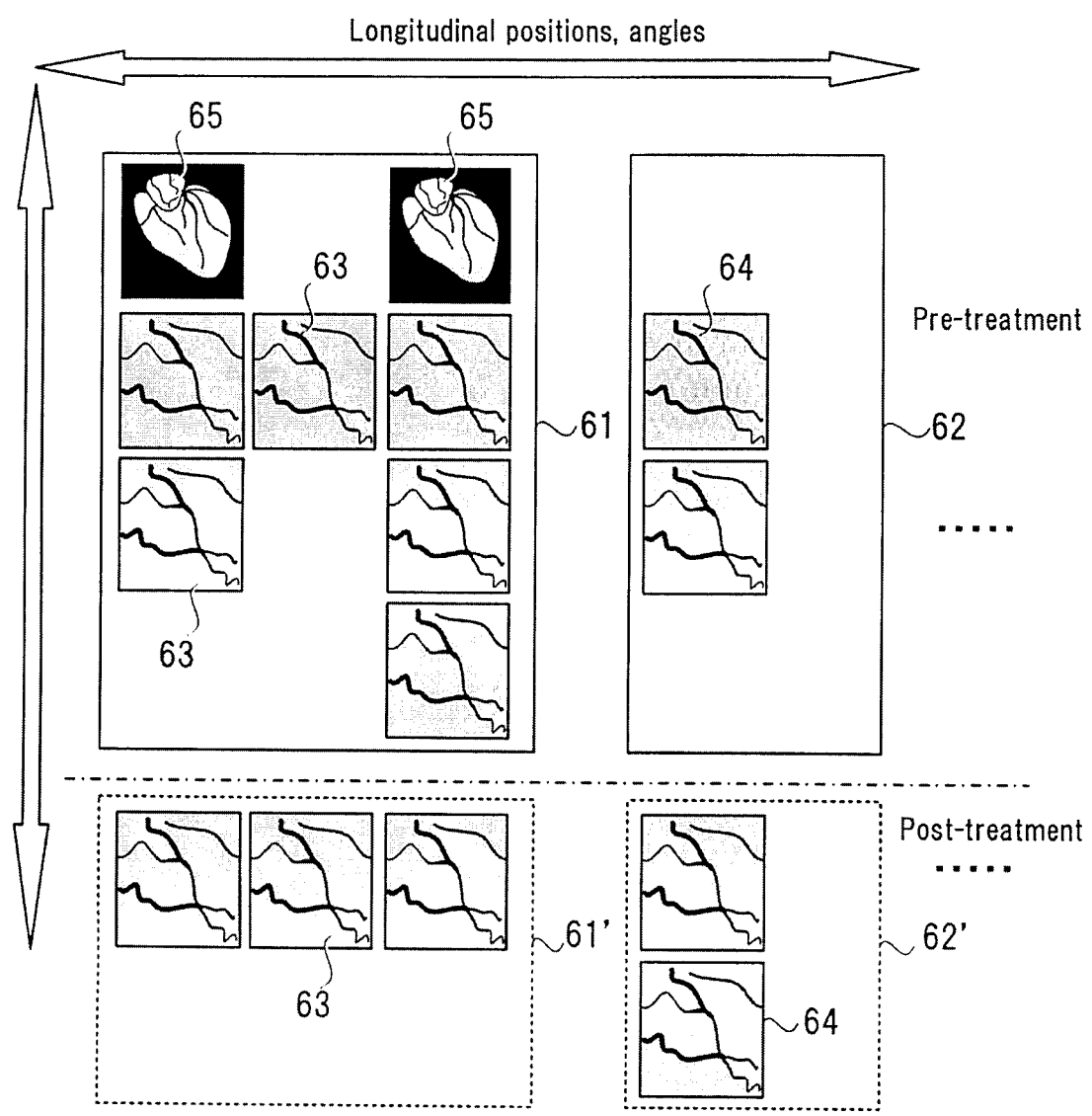
FIG. 13 is an explanatory diagram showing an example of adding an image obtained by another imaging device and displaying.

FIG. 13 shows still another display example of the fourth embodiment. In FIG. 13, as opposed to the display example of FIG. 11, CT images 65 taken by still another imaging device, which is for example a CT device, are extracted on a per-imaging-angle basis and turned into thumbnails, and are arranged and displayed together with images taken by the angiography device 100. CT images and other images from another imaging device are supplied to the storage unit 32, in which the images are stored.

Displaying the CT images 65 makes it easier to weigh inspection images against previously taken CT images. Moreover, it is possible to figure out which part of a blood vessel becomes clogged, and how seriously a blood vessel becomes clogged after recognizing the shape (circular, oval or any other shape) of the blood vessel and other factors. Therefore, the CT images 65 can be a guide to determine an angular direction in order to view an image taken from the angular direction.

Figure 14:
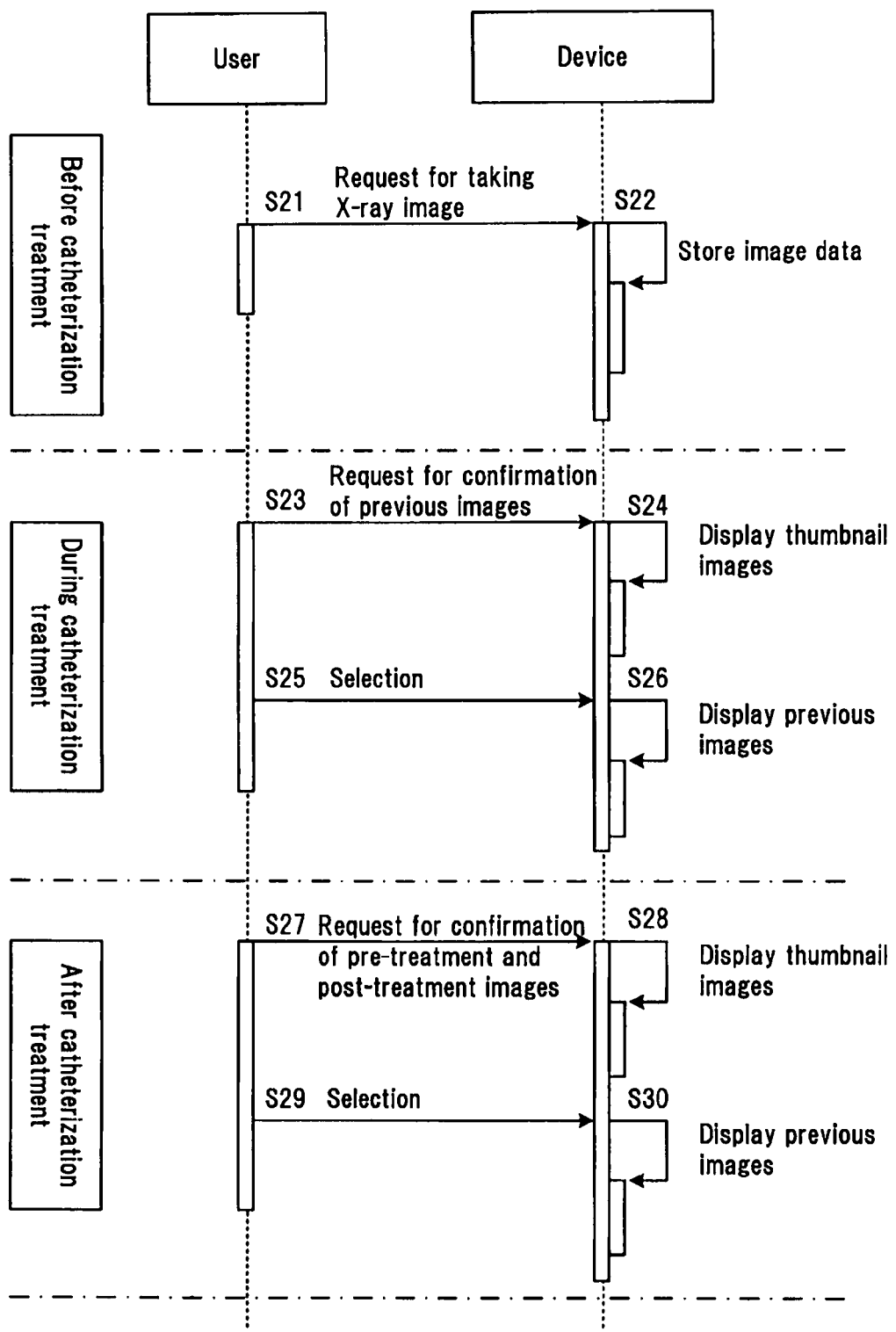
FIG. 14 is a sequence chart showing an example of displaying an image in a catheterization treatment.

FIG. 14 is a sequence chart showing the case where, in a catheterization treatment, thumbnail images are displayed as shown in FIG. 11 (or FIG. 12). FIG. 14 shows operations of a user (doctor or the like) and the X-ray image diagnosis device 100 (referred to as device) before the catheterization treatment (pre-operation examination), during the catheterization treatment, and after the catheterization treatment.

Before the catheterization treatment, a user at step S21 requests the device to take an X-ray image. The device at step S22 takes an X-ray image, and stores image data, which are the imaging results, in the storage unit 32. During the catheterization treatment, the user at step S23 makes a request for confirmation of previously taken images. The device at step S24 generates and displays thumbnail images. When the user at step S25 selects one from among the thumbnail images, the device displays the details of the selected previously taken image at step S26. At this stage, the user references the previous image and carries out the catheterization treatment. After the catheterization treatment, an X-ray image is taken, and image data are stored in the storage unit 32.

After the catheterization treatment, when a request for confirmation of pre-treatment and post-treatment images is made from the user at step S27, the device at step S28 generates and displays thumbnail images. At this time, as shown in FIG. 11, pre-treatment and post-treatment thumbnail images are displayed. The thumbnail images are classified into regions and displayed on a per-imaging-angle basis. At step S29, when the user selects an arbitrary thumbnail image, image data corresponding to the selected thumbnail image are enlarged and displayed at step S30, thereby making it possible to confirm healing levels. Incidentally, at step S28, the thumbnail images shown in FIG. 12 or 13 may be displayed.

Incidentally, the following supplements the information of each of the above-described embodiments. As for an image to be stored in the storage unit 32, an imaging angle and imaging time are added to image data before the image data are stored. A judgment may be made as to whether image data are pre-treatment or post-treatment data on the basis of device information on the image or information about angiogram/blood flow and the like, and information about the judgment may be added to the image data before the image data are stored. Alternatively, the user may input pre-treatment time and post-treatment time, and time information may be added to the image data.

Moreover, the values of the following factors and other values at the time of imaging may be recorded, the angle of the C-arm 24, the position of the arm (the position of the ceiling), the position of the bed, and the position and direction of a patient. Then, the recorded information may be stored along with image data. Moreover, information about the following factors and other kinds of information may also be stored, an imaging time, FOV (field-of-view size), a zooming level, an imaging program name, the flow rate and time of a contrast medium previously used, and a history of having or not having stricture.

Moreover, information about the following factors and other kinds of information may be stored, the cumulative traveling distances of the arm's position and bed's position (which are not taken into account if the arm and the bed do not move beyond a certain distance), the cumulative amount of change in the arm's angle (which is not taken into account if the arm does not rotate beyond a certain point), and a varying threshold value of the arm's angle (which is not taken into account if the threshold value does not go beyond a certain value).

The above has described an example in which, when a table of thumbnail images is displayed, a 3D or 2D human body model is used. However, after a rough location is selected from a 3D human body model, a 2D human body model of a region thereof may be displayed before thumbnail images are displayed. Moreover, the thumbnail images that are displayed in a table format may be rearranged under a certain condition (parameter) before being sorted and displayed.

In an X-ray image diagnosis device having two C-arms, front-plane and side-plane images (Bi-Plane Images) may be stored, depending on an imaging region, or in the case of the heart for example, front-plane and side-plane thumbnail images may be displayed separately, since a cerebral blood vessel needs to be viewed from both directions, front-plane and side-plane thumbnail images may be displayed in pairs. If the thumbnail images are displayed in pairs, a link may be established from one image to the other image, or both images may be displayed side by side. Moreover, within a front-plane thumbnail image, a side-plane thumbnail image may be displayed as a sub-screen. Alternatively, within a side-plane thumbnail image, a front-plane thumbnail image may be displayed as a sub-screen.

As described above, according to the embodiments of the present invention, thumbnail images are displayed for each of the imaging ranges specified. Therefore, requested image data can be easily found. Moreover, the following are added to taken image data: an imaging angle, an imaging time, and time-segment data about pre- and post-treatment or about pre- and post-treatment by a user. Therefore, based on the above information, thumbnail images can be displayed in chronological order.

Incidentally, what is described of the above embodiments is an example in which the flat panel detector 21 is used for the X-ray detection unit 20. However, instead of the flat panel detector 21, an X-ray detection unit including X-ray I.I. (Image Intensifier) and an X-ray TV camera may be used. According to an imaging method in which the X-ray I.I. is used, X-ray image information that is obtained after X-rays have passed through a subject is converted into an optical image in the X-ray I.I. The optical image is then captured by the X-ray TV camera and converted into electric signals. The X-ray image information that has been converted into electric signals is displayed on a monitor of a display unit after A/D conversion is performed.

While certain embodiments of the inventions have been described, these embodiments have been presented by way of example only, and are not intended to limit the scope of the inventions. Indeed, the novel devices and methods described herein may be embodied in a variety of the other forms; furthermore, various omissions, substitutions and changes in the form of the apparatus and methods described herein may be made without departing from the sprit of the inventions. The accompanying claims and their equivalents are intended to cover such forms or modifications as would fall within the scope and spirit of the inventions.

REFERENCE SIGNS LIST

100: X-ray image diagnosis device (angiography device)
10: X-ray generation unit 11: X-ray tube
20: X-ray detection unit
21: Flat panel detector
24: C-arm
25: Top panel
26: Imaging unit
31: Image data processing unit
32: Storage unit
33: System control unit
34: Operation unit
35: Display unit
39: Bus line
40: Transfer mechanism unit

The invention claimed is:

1. A medical image diagnosis device, comprising:
processing circuitry that
    takes an image of a subject, with an X-ray generation device which exposes the subject to X-rays and an X-ray detector which detects X-rays that have passed through the subject, being supported on a supporter, and
    controls so as to rotate and move the supporter with respect to the subject and take images at a plurality of imaging ranges of the subject from a plurality of viewpoints;
a memory that stores image data taken from a plurality of the viewpoints; and
an interface device that selects a desired imaging range from among the plurality of imaging ranges, on a human body model displayed on a display device, wherein
the human body model is divided into at least three regions in a cranio-caudal direction, and is divided into at least three regions in a direction perpendicular to the cranio-caudal direction in order to set a plurality of angular directions with matrix-like segments, and the interface device specifies one from the plurality of angular directions to select the imaging range,
the processing circuitry classifies a plurality of pieces of the image data stored in the memory into the plurality of imaging ranges to generate thumbnail images, and outputs the thumbnail images within the desired imaging range selected by the interface device, and
the display device displays the thumbnail images within the desired imaging range output from the processing circuitry with the human body model.

2. The device according to claim 1, wherein
the processing circuitry sets a plurality of the viewpoints to take images of the subject from a plurality of angular directions.

3. The device according to claim 2, wherein,
when there are image data taken from a plurality of angular directions, the processing circuitry disposes the thumbnail images in areas that are each classified by imaging range.

4. The device according to claim 1, wherein
the processing circuitry sets a plurality of the viewpoints to take images of the subject from a plurality of positions along a body-axis direction.

5. The device according to claim 1, wherein
the interface device rotates a three-dimensional human body model displayed on the display device and specifies an arbitrary viewpoint in order to select the imaging range.

6. The device according to claim 1, wherein,
when there is a plurality of thumbnail images in the selected imaging range, the processing circuitry arranges and disposes the thumbnail images in chronological order.

7. The device according to claim 6, wherein
the processing circuitry generates a thumbnail image selected from among the thumbnail images arranged in chronological order in such a way that the selected thumbnail image can be distinguished from other thumbnail images when being displayed.

8. The device according to claim 1, wherein,
when one of the thumbnail images displayed on the display device is selected, the processing circuitry enlarges corresponding image data before supplying the image data to the display device.

9. The device according to claim 1, wherein,
when there are image data of a selected region taken from a plurality of viewpoints, the processing circuitry generates thumbnail images corresponding to the imaging viewpoints before supplying the thumbnail images to the display device.

10. The device according to claim 1, wherein
the processing circuitry divides the imaging ranges of the subject into regions, generates thumbnail images for each of a plurality of imaging angles on the basis of the image data within the divided imaging ranges, and disposes the thumbnail images in chronological order in a way that makes comparison possible.

11. The device according to claim 10, wherein
the memory stores image data obtained by another imaging device, and the processing circuitry adds a thumbnail image of the obtained image data to thumbnail images classified by region of the subject.

12. The device according to claim 1, wherein
the processing circuitry divides the imaging ranges of the subject into regions, generates thumbnail images for each of a plurality of imaging angles on the basis of the image data within the divided imaging ranges, and disposes pre-treatment and post-treatment thumbnail images in chronological order in a way that makes comparison possible.

13. A medical image processing method for a device that includes an imaging device that takes an image of a subject, with an X-ray generation device which exposes the subject to X-rays and an X-ray detector which detects X-rays that have passed through the subject, being supported on a supporter, the medical image processing method comprising:
rotating and moving the supporter with respect to the subject and taking images at a plurality of imaging ranges of the subject from a plurality of viewpoints;
storing in a memory image data taken from a plurality of the viewpoints;
displaying a human body model on a display device, the human body model being divided into at least three regions in a cranio-caudal direction, and being divided into at least three regions in a direction perpendicular to the cranio-caudal direction in order to set a plurality of angular directions with matrix-like segments;
selecting, by an interface device, a desired imaging range from among the plurality of imaging ranges on the human body model by specifying one from the plurality of angular directions;
classifying a plurality of pieces of the image data into the plurality of imaging ranges to generate thumbnail images;
outputting the thumbnail images within the desired imaging range selected by the interface device; and displaying the thumbnail images within the desired imaging range on the display device with the human body model.

14. The medical image processing method according to claim 13, further comprising adding, to the image data, imaging angle data, imaging time data, and time-segment data related to pre-treatment and post-treatment.

* * * * *